US012213929B2

(12) United States Patent
Dixon et al.

(10) Patent No.: US 12,213,929 B2
(45) Date of Patent: Feb. 4, 2025

(54) METHOD, APPARATUS, AND SYSTEM FOR TELEOPERATED, MOTORIZED REHABILITATIVE CYCLING

(71) Applicant: UNIVERSITY OF FLORIDA RESEARCH FOUNDATION, INCORPORATED, Gainesville, FL (US)

(72) Inventors: Warren E. Dixon, Gainesville, FL (US); Kimberly J. Stubbs, Middleburg, FL (US); Brendon Allen, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 800 days.

(21) Appl. No.: 17/449,159

(22) Filed: Sep. 28, 2021

(65) Prior Publication Data

US 2022/0104989 A1 Apr. 7, 2022

Related U.S. Application Data

(60) Provisional application No. 63/086,394, filed on Oct. 1, 2020.

(51) Int. Cl.
*A61H 1/02* (2006.01)
*A61N 1/36* (2006.01)

(52) U.S. Cl.
CPC ......... *A61H 1/0214* (2013.01); *A61H 1/0274* (2013.01); *A61N 1/36003* (2013.01);
(Continued)

(58) Field of Classification Search
CPC .......... A61H 1/00–0296; A61H 1/0214; A61N 1/00–445; A61N 1/36003;
(Continued)

(56) References Cited

U.S. PATENT DOCUMENTS 5,466,213 A * 11/1995 Hogan .................... A61H 1/02 482/901
2006/0247095 A1* 11/2006 Rummerfield ....... A61H 1/0214 482/57

(Continued)

OTHER PUBLICATIONS

Wang X, Leung KW, Fang Y, Chen S, Tong RK. Design of Functional Electrical Stimulation Cycling System for Lower-Limb Rehabilitation of Stroke Patients. Annu Int Conf IEEE Eng Med Biol Soc. Jul. 2018;2018:2337-2340. doi: 10.1109/EMBC.2018.8512869. PMID: 30440875. (Year: 2018).*

(Continued)

*Primary Examiner* — Valerie L Woodward
*Assistant Examiner* — Paige Kathleen Bugg
(74) *Attorney, Agent, or Firm* — ALSTON & BIRD LLP

(57) ABSTRACT

Provided herein is a method, apparatus, and system for teleoperated, functional electric stimulation actuated rehabilitative cycling. Methods may include: receiving, at a master system, rotational input generating master system sensor input having a master system cadence; providing the master system sensor input including the master system cadence to a controller based on the rotational input from a rehabilitation participant or a remote therapist received at the master system; receiving, at a slave system, rotational input from the rehabilitation participant generating slave sensor input having a slave system cadence; providing the slave system sensor input including the slave system cadence to the controller based on the rotational input from the participant received at the slave system; and providing, from the controller, feedback through the master system in response to a difference between the master system cadence and the slave system cadence.

17 Claims, 9 Drawing Sheets

250
200
264
256
252
254
258
260

(52) U.S. Cl.
CPC ...... *A61N 1/36031* (2017.08); *A61H 2201/10* (2013.01); *A61H 2201/1215* (2013.01); *A61H 2201/501* (2013.01); *A61H 2201/5064* (2013.01)

(58) Field of Classification Search
CPC ...... A61N 1/36031; A63B 22/06–0694; A63B 2022/0611–0688; A63B 69/16; A63B 2069/161–168; A63B 24/0087
USPC ............................................. 601/15, 29, 36
See application file for complete search history.

(56) References Cited

U.S. PATENT DOCUMENTS

2015/0165265 A1* 6/2015 Tholkes .............. A61H 1/0262 482/57
2017/0157396 A1* 6/2017 Dixon ................. A61N 1/0452
2021/0134457 A1* 5/2021 Mason .................... A61H 1/02
2021/0228862 A1* 7/2021 Campos Uribe .. A61N 1/36034

OTHER PUBLICATIONS

V. H. Duenas, C. A. Cousin, A. Parikh, P. Freeborn, E. J. Fox and W. E. Dixon, “Motorized and Functional Electrical Stimulation Induced Cycling via Switched Repetitive Learning Control,” in IEEE Transactions on Control Systems Technology, vol. 27, No. 4, pp. 1468-1479, Jul. 2019 (Year: 2019).*

C.A. Rouse, C.A. Cousin, B.C. Allen, and W.E. Dixon. “Split-Crank Cadence Tracking for Switched Motorized FES-Cycling with Volition Pedaling”. pp. 4393-4398 of American Control Conference 2019. Conference held Jul. 10, 2019-Jul. 12, 2019. Added to IEEE Aug. 29, 2019. (Year: 2019).*

* cited by examiner $$\underbrace{B_M u_s}_{131} + \underbrace{B_{e_l} u_{e_l}}_{132} + \underbrace{\tau_{vol_l}}_{133} = \underbrace{M_l \ddot{q}_l}_{134} + \underbrace{V_l \dot{q}_l}_{135} + \underbrace{b_{c_l} \dot{q}_l}_{136} + \underbrace{G_l}_{137} + \underbrace{P_l}_{138} + \underbrace{d_{c_l} + d_{r_l}}_{139}$$

FIG. 3

$$\underbrace{B_{e_{mc}} u_{e_{mc}}}_{141} + \underbrace{\tau_{vol_{mc}}}_{142} = \underbrace{M_{mc}\ddot{q}_{mc}}_{143} + \underbrace{V_{mc}\dot{q}_{mc}}_{144} + \underbrace{b_{c_{mc}}\dot{q}_{mc}}_{145} + \underbrace{G_{mc}}_{146} + \underbrace{P_{mc}}_{147} + \underbrace{d_{c_{mc}} + d_{r_{mc}}}_{148}$$

FIG. 4

METHOD, APPARATUS, AND SYSTEM FOR TELEOPERATED, MOTORIZED REHABILITATIVE CYCLING

CROSS-REFERENCE TO RELATED APPLICATIONS

This application claims priority to U.S. Provisional Patent Application Ser. No. 63/086,394, filed on Oct. 1, 2020, the contents of which are hereby incorporated by reference in their entirety

STATEMENT OF GOVERNMENT FUNDING

This invention was made with government support under 1762829 awarded by the national Science Foundation. The government has certain rights in this invention.

TECHNOLOGICAL FIELD

An example embodiment of the present disclosure relates to a method, apparatus, and system for functional electric stimulation rehabilitation, and more particularly, to a method, apparatus, and system for teleoperated, motorized functional electric stimulation actuated rehabilitative cycling.

BACKGROUND

Many people are affected by a wide range of neuromuscular disorders, many of which can be improved through the use of Functional Electrical Stimulation (FES) rehabilitative cycling. FES is a rehabilitation technique used for people with neuromuscular disorders (NDs) such as a stroke or spinal cord injury. FES rehabilitation using a stationary cycle has been shown to have significant psychological benefits, motivating the desire to extend the duration and the efficiency of FES rehabilitative cycling. The addition of coordinated movement between upper limbs and lower limbs in rehabilitation can have a positive effect on neural plasticity leading to faster restoration of walking in those who have some neurological and/or neuromuscular disorders. By coordinating rhythmic arm and leg movements on a cycle, walking can be improved for stroke patients. This coordination might also serve to improve neural plasticity as neural connections are thought to exist between upper and lower limbs. Further, motor recovery can be improved with specific, repetitive movement that is enjoyable for the participant and has a positive emotional impact. For those with neurological disorders, rehabilitation is often a long process that should continue after the participant has left the hospital environment such that ideally, rehabilitative therapy is available in the home environment. However, rehabilitation is often not completed when unsupervised as participants do not find the rehabilitative technology to be motivating enough to encourage them to continue their treatment.

BRIEF SUMMARY

Embodiments of the present disclosure provide a method, apparatus, and system for bilateral teleoperation system for a coordinated upper and lower body rehabilitative FES cycling. Embodiments provided herein include a system for rehabilitation including: a master controller system where the master controller system is configured to be driven by a master system operator's volitional efforts; a leg-cycle system including a motor, where the leg-cycle system is configured to be driven by both functional electric stimulation of a rehabilitation participant and the motor; and a controller for receiving sensor input from the master controller system and to control driving of the leg-cycle system with the motor and the application of functional electric stimulation responsive to sensor input from the master controller system. The controller may be configured to apply a variable operator to the motor input of the leg-cycle system during functional electric stimulation.

According to some embodiments, the controller controls driving of the leg-cycle system using the motor responsive to sensor input from the master controller system to generate position and velocity of the leg-cycle system based on the position and velocity of the master controller system. The controller may apply resistive motor effort to the master controller system indicative of a difference between operation of the master controller system and the leg-cycle system by the participant. The leg-cycle system may be a split-crank leg-cycle system whereby two legs of a rehabilitation participant can pedal the leg-cycle system independently. Embodiments may include a controller having a communications module for receiving control signals from a remotely located therapist, where the control signals from the remotely located therapist act as the master system to the participant leg-cycle, and haptic feedback is returned to the remote therapist master system indicative of a difference between desired and actual operation at the rehabilitation participant system.

Embodiments provided herein may include a method for rehabilitation including: receiving, at a master controller system, rotational input from a participant producing a master controller cadence; providing master controller input including the master controller cadence to a controller based on the rotational input from the participant received at the master controller system; receiving, at a leg-cycle system, rotational input from a participant having a leg-cycle cadence; providing leg-cycle input including the leg-cycle cadence to the controller based on the rotational input from the participant received at the leg-cycle system; and providing, from the controller, feedback through at least one of the master controller system or the leg-cycle system in response to a difference between the master controller cadence and the leg-cycle cadence, where rotation of the master controller system and rotation of the leg-cycle system are not mechanically coupled. Methods may include providing a signal to a motor coupled to the leg-cycle system to provide motor assistance during periods of functional electric stimulation (FES) to the participant. Methods may include transmitting at least one of master controller feedback or leg-cycle feedback to a remotely located therapist; and receiving input to the controller to control haptic feedback to the master controller system. Methods may include transmitting at least one of master controller feedback or leg-cycle feedback to a remotely located therapist; and receiving input to the controller to control motor input to the leg-cycle system.

Embodiments provided herein may include a method for rehabilitation including: receiving, at a master system, rotational input generating master system sensor input having a master system cadence; providing the master system sensor input including the master system cadence to a controller based on the rotational input from a rehabilitation participant or a remote therapist received at the master system; receiving, at a slave system, rotational input from the rehabilitation participant generating slave sensor input having a slave system cadence; providing the slave system sensor input including the slave system cadence to the controller based on the rotational input from the participant received at the slave system; and providing, from the controller, feedback through the master system in response to a difference between the master system cadence and the slave system cadence, where rotation of the master system and rotation of the slave system are not mechanically coupled.

According to example embodiments, methods may include providing a signal to a motor coupled to the slave system based on rotational input at the master system. Methods may include transmitting feedback to the master system operated by the rehabilitation participant or a remotely located therapist; and receiving input to the controller to control haptic feedback to the master system. Methods may include transmitting feedback from the master system to the slave system; and receiving input to the controller to control motor input to the slave system. The master system may include a hand-cycle system and the slave system may include a leg-cycle system.

Embodiments of the present disclosure provide a system for rehabilitation including: a master system driven by a master system operator's volitional efforts, where the master system includes at least one of a hand-cycle system or a leg-cycle system; a slave system driven by a rehabilitation participant's functional electric stimulation actuated muscle effort and a motor, where the slave system includes at least one of a hand-cycle system or a leg-cycle system; and a controller for receiving sensor input from the slave system and to control driving of the slave system by the motor responsive to sensor input from the master system. The controller may apply a variable operator to the motor of the slave system during functional electric stimulation.

According to some embodiments, the controller controls driving of the slave system by the motor and the functional electric stimulation actuated muscle effort responsive to sensor input from the master system to generate position and velocity of the slave system based on the position and velocity of the master system. The controller may control resistive motor input applied to the master system indicative of a difference between operation of the master system and the slave system. The slave system may include a split-crank leg-cycle system where two legs of a participant pedal the leg-cycle system independently. The controller may include a communications module for communicating between the master system and the slave system, where the master system is located remotely from the slave system, and where the master system provides haptic feedback based on sensor input received at the slave system.

BRIEF DESCRIPTION OF DRAWINGS

FIG. 3 illustrates a dynamic model equation for modeling leg-cycle dynamics according to an example embodiment of the present disclosure;

FIG. 4 illustrates a dynamic model equation for modeling master controller dynamics of a master controller system according to an example embodiment of the present disclosure;

DETAILED DESCRIPTION

Figure 1:
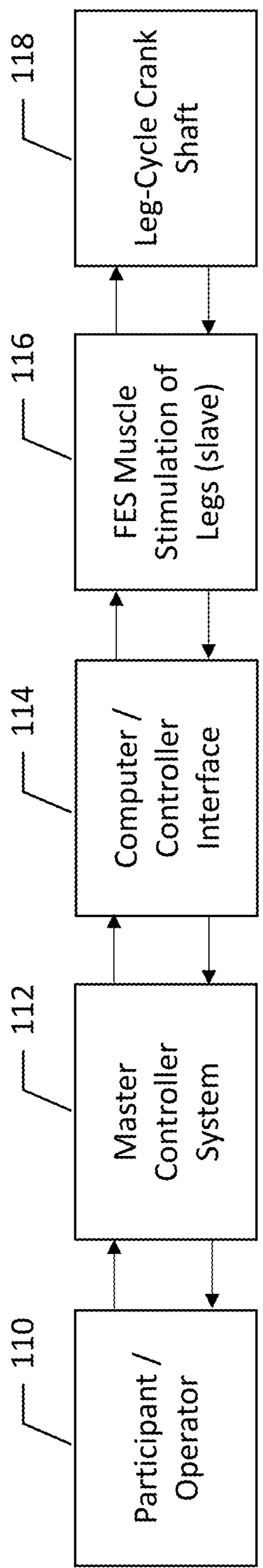
FIG. 1 illustrates an example bilateral teleoperation system for a coordinated upper and lower body rehabilitative FES cycling system according to an embodiment of the present disclosure.

Some example embodiments of the present disclosure will now be described more fully hereinafter with reference to the accompanying drawings, in which some, but not all embodiments of the invention are shown. Indeed, various embodiments of the disclosure may be embodied in many different forms and should not be construed as limited to the example embodiments set forth herein; rather, these example embodiments are provided so that this disclosure will satisfy applicable legal requirements. Like reference numerals refer to like elements throughout.

Neuromuscular disorders can occur when impulses from the brain to muscle groups is disrupted. These neuromuscular disorders cause limited mobility and can cause a reduced quality of life. Functional Electric Stimulation (FES) rehabilitation can increase mobility and improve the quality of life for those suffering from neuromuscular disorders. FES includes the application of an electric field directly to muscle groups to cause involuntary actuation of the muscle. This stimulation results in physiological and psychological benefits while providing motivation to extend duration of rehabilitation therapy and improve efficiency of the therapy.

Embodiments of the present disclosure include a method, apparatus, and system for functional electric stimulation (FES) rehabilitation, and more particularly, to a method, apparatus, and system for teleoperated, motorized functional electric stimulation actuated rehabilitative cycling. Embodiments described herein implement coordinated motion during rehabilitation using a strongly coupled bilateral telerobotic system between a master system driven by an operator's volitional efforts, where the operator may be a rehabilitation participant or a remote therapist, and a split-crank leg-cycle system driven by the switched application of FES muscle actuation and motor effort. A variable operator is applied to the leg-cycle's motor input during the FES stimulation regions to provide assistance as required. Lyapunov-based analysis methods are used on the combined leg and hand-cycle system to prove global exponential stability. Further, all switched system inputs are bounded, thus the states of the telerobotic master (i.e., the hand-cycle system) is bounded such that the telerobotic system is stable.

Figure 2:
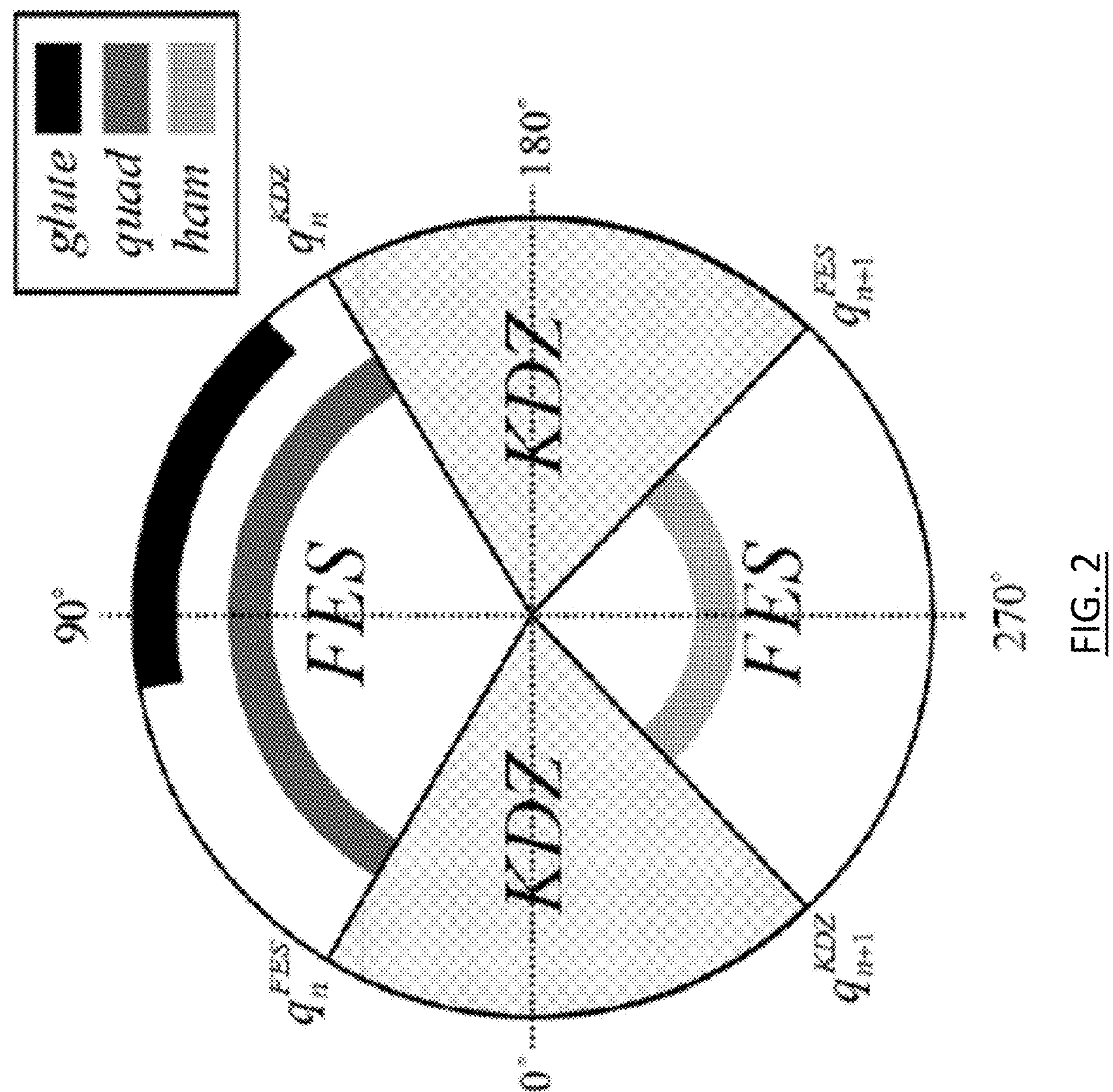
FIG. 2 illustrates an example embodiment of a rotation cycle where portions of the cycle are in kinematic dead zones (KDZ), while the other portions of the cycle employ functional electric stimulation (FES) according to an example embodiment of the present disclosure.

FIG. 2 illustrates an example embodiment of a rotation cycle where portions of the cycle are in kinematic dead zones (KDZ), while the other portions of the cycle employ functional electric stimulation (FES). These FES portions of the cycle employ different muscles and muscle groups, such as the glute, quadricep (quad), and hamstring muscles. The transition between the KDZ and the FES is denoted with angles, such as $q_n^{FES}$ where the KDZ transitions to the FES using the quad and later the glute, with $q_n^{KDZ}$ being the transition point back to the KDZ. Angle $q_{n+1}^{FES}$ is the transition from the KDZ to the FES portion of the cycle employing the hamstring, while $q_{n+1}^{KDZ}$ transitions back to the KDZ.

According to example embodiments described herein, the rehabilitation participant is not expected to produce volitional efforts at the slave system (e.g., a leg-cycle system or hand-cycle system), rather all intended rehabilitation participant effort is activated by the FES applied across the muscles of the participant (e.g., the leg muscles for a leg-cycle slave system). A controller, as detailed further below, determines the FES application in response to sensor input from the master system.

FES rehabilitation techniques are beneficial for people with neurological disorders including neuromuscular disorders, such as stroke or spinal cord injuries. FES rehabilitation using a stationary cycle has significant physiological and psychological benefits motivating the desire to extend the duration and efficiency of the FES rehabilitative cycling. Embodiments described herein employ Lyapunov-based, non-linear control to adapt for unknown parameters and to switch between FES activated muscle effort and motor assistance to ensure that muscle groups are only stimulated in efficient force production regions of a crank rotation of the cycle, thereby delaying muscle fatigue and extending rehabilitative dosage.

When rehabilitation participants are left to complete rehabilitation on their own, participants often fail to complete rehabilitation due to lack of motivation, level of difficulty, or a lack of immediately recognized benefit. While physical rehabilitation with an in-person, hands-on clinician benefits from the ability of the clinician to feel areas of limited range of motion and directly determines performance. Remote therapy has limited benefit as a clinician cannot effectively determine range of motion and strength of a patient. This has led to the creation of teleoperative and/or game-based rehabilitative systems that provide feedback to the clinician from the patient during remote therapy sessions. These systems inform participants of the desired performance, generally using impedance control as determined by a remote therapist or computer-based system.

Embodiments provided herein improve upon teleoperative-based rehabilitation systems with FES rehabilitative cycling with added coordination through the implementation of a robust, bilateral, strongly coupled teleoperation system where the rehabilitation participant, or a clinician, pedals an uncoupled master controller system by their volitional efforts and the FES and motor actuated, switched leg-cycle system acts as the telerobotic slave. The master controller system of an example embodiments includes a hand-cycle system. FIG. 1 illustrates an example bilateral teleoperation system for a coordinated upper and lower body rehabilitative FES cycling system including a participant/operator 110. Using this telerobotic system, rehabilitative participants feel as though they have an improved ability to choose their desired position and cadence for the entire cycle-rider system; thus, improving their motivation and compliance for home therapies.

According to example embodiments disclosed herein, for the telerobotic system to produce the desired beneficial coordination of the hands and legs, a strong coupling between the systems has been developed so that the slave (leg-cycle crank shaft 118 and FES stimulation of legs 116 of FIG. 1) closely mimic the position and velocity of the master controller system 112. To ensure that each leg is closely coordinated with its paired hand and to address the needs of participants with asymmetric impairments, the leg-cycle system of example embodiments is a split-crank design where each leg can independently drive the crank shaft. The resistive control input applied to the master controller system 112 informs the participant of the error between the desired position (e.g., set by a hand-crank angle of the master controller system) and the actual position of the associated leg-cycle system. By reflecting feedback from the leg-cycle system to the master system input, the participant will adjust their cadence allowing for a closed-loop cyber-physical human machine interaction.

Embodiments provided herein include a controller 114 developed for a split-crank leg-cycle system that yields larger cadence and position tracking errors than typical for a mechanically coupled crank/pedal set. This is in part due to during split-crank operation, when the leg travels through a return phase of the rotation (e.g., in the hamstring muscle group stimulation region), there is no assistance provided by the drive phase of the opposing leg (e.g., in the quadriceps femoris muscle group stimulation region), thus requiring a significant amount of effort from the hamstring muscle group. This additional effort without motor assistance may lead to FES input saturation causing rapid muscle fatigue and participant discomfort. Further, in split-crank systems hand-cycle and leg-cycle systems can become out-of-phase, leading to a reduction in the possible benefit of coordinated effort. Therefore, embodiments described herein introduce variable motor effort within the stimulation regions to delay the onset of fatigue, increasing participant comfort, and improving the position and cadence tracking to extend the rehabilitative dosages and participation.

Dynamic Models—Lower Body Leg-Cycle System

Using a split-crank cycle, the dynamics of a single side of the split-crank cycle and corresponding controlling hand-cycle are modeled independently from the opposing side without loss of generality. The cycle-rider lower body switched dynamics for one side may be modeled as:

$$\tau_{el}=\tau_{cl}(q_l,\dot{q}_l,\ddot{q}_l,t)+\tau_{rl}(q_l,\dot{q}_l,\ddot{q}_l,t) \tag{1}$$

Where $q_l$: $\mathbb{R}_{\geq 0}\rightarrow Q_l$ denotes the angular position and $Q_l \subseteq \mathbb{R}$ is the set of all possible measurable leg-cycle crank angles. The measured angular velocity of the leg-cycle crank arm is denoted by $\dot{q}_l$: $\mathbb{R}_{>0}\rightarrow\mathbb{R}$ and the unmeasurable angular acceleration is denoted by $\ddot{q}_l$: $\mathbb{R}_{>0}\rightarrow\mathbb{R}$. In expression (1) above, $\tau_{el}$: $Q_l\times\mathbb{R}\times\mathbb{R}\times\mathbb{R}_{\geq 0}\rightarrow\mathbb{R}$ represents the electric motor torque, $\tau_{cl}$: $Q_l\times\mathbb{R}\times\mathbb{R}\times\mathbb{R}_{\geq 0}\rightarrow\mathbb{R}$ represents the cycle torque, and $\tau_{rl}$: $Q_l\times\mathbb{R}\times\mathbb{R}\times\mathbb{R}_{\geq 0}\rightarrow\mathbb{R}$ represents the rider toque. The unknown linear dynamics for the leg cycle are:

$$\tau_{cl}(q_l,\dot{q}_l,\ddot{q}_l,t)=J_{cl}(q_l)\ddot{q}_l+b_{cl}\dot{q}_l+d_{cl}(t) \tag{2}$$

Where the inertial effects, viscous damping effects, and disturbances are denoted by $J_{cl}$: $Q_l\rightarrow\mathbb{R}$, $b_{cl}\in\mathbb{R}_{\geq 0}$, and $d_{cl}$: $\mathbb{R}_{\geq 0}\rightarrow\mathbb{R}$, respectively. The rider torque in (1) can be divided into its passive elements, $\tau_p$: $Q_l\times\mathbb{R}\times\mathbb{R}\rightarrow\mathbb{R}$, the torques produced by muscle forces, $\tau_M$: $Q_l\times\mathbb{R}\times\mathbb{R}_{\geq 0}\rightarrow\mathbb{R}$, and rider disturbances, $d_{rl}$: $\mathbb{R}_{\geq 0}\rightarrow\mathbb{R}$, such that:

$$\tau_{rl}(q_l,\dot{q}_l,\ddot{q}_l,t)=(q_l,\dot{q}_l,\ddot{q}_l)-\tau_M(q_l,\dot{q}_l,t)+d_{rl}(t) \tag{3}$$

The passive rider dynamics in expression (3) are modeled by:

$$\tau_{pl}(q_l,\dot{q}_l,\ddot{q}_l)=M_{pl}(q_l)\ddot{q}_l+V_l(q_l,\dot{q}_l)\dot{q}_l+G_l(q_l)+P_l(q_l,\dot{q}_l) \tag{4}$$

where $M_{pl}$: $Q_l\rightarrow\mathbb{R}$, $V_l$: $Q_l\times\mathbb{R}\rightarrow\mathbb{R}$, $G_l$: $Q_l\rightarrow\mathbb{R}$ and $P_l$: $Q_l\times\mathbb{R}\rightarrow\mathbb{R}$ represent the unknown, nonlinear inertial effects, centripetal-Coriolis effects, gravitational effects, and passive viscoelastic muscle forces. The muscle torques in expression (3) are modeled as the summation of all induced muscle forces from individually stimulated muscle groups plus volitional efforts, denoted by $\tau_{vol_l} \in \mathbb{R}_{\geq 0}$, such that:

$$\tau_M(q_l,\dot{q}_l,t)=\Sigma_{m\in M}B_{ml}(q_l,\dot{q}_l)u_{ml}(q_l,t)+\tau_{vol_l} \quad (5)$$

where the subscript $m \in M=\{Q, G, H\}$ indicates the quadriceps femoris (Q), gluteal (G), and hamstring (H) muscle groups. The unknown, nonlinear muscle control effectiveness in (5) is denoted by $B_{ml}$: $Q_l \times \mathbb{R} \rightarrow \mathbb{R}_{\geq 0}$, $\forall m \in M$ and the designed FES muscle control input (i.e., pulse width) is denoted by $u_{ml}$: $Q_l \times \mathbb{R}_{\geq 0} \rightarrow \mathbb{R}$. The portion of the set $Q_l$ where each muscle group is stimulated is denoted by $Q_m \subset Q_l$ such that:

$$Q_m \triangleq \{q_l \in Q_l | T_m(q_l) > \varepsilon_m\} \quad (6)$$

where $\varepsilon_m \in (0, \max(T_m))$ represents a user-defined lower threshold for each muscle group's torque transfer ratio, $T_m$: $Q_l \rightarrow \mathbb{R}$ such that each muscle group's contribution only acts to produce positive crank rotation. The region about the crank cycle where FES of at least one muscle group produces a positive crank is denoted by $Q_{FES} \triangleq \cup_{m\in M}\{Q_m\}$, $\forall m \in M$.

The level of stimulation intensity applied to each muscle group is defined as:

$$u_m \triangleq \sigma_m(q_l)k_m u_s(t) \quad (7)$$

$\forall m \in M$, where $k_m \in \mathbb{R}_{\geq 0}$ is a selectable constant associated with participant comfort level during stimulation, $u_s$ (t) represents the subsequently designed FES control input, and $\sigma_m$ denotes a switching signal determined from (6), where $\sigma_m$: $Q_l \rightarrow \{0,1\}$ such that:

$$\sigma_m \triangleq \begin{cases} 1 \text{ if } q_l \in Q_m \\ 0 \text{ if } q_l \notin Q_m \end{cases}. \quad (8)$$

The electric motor torque produced about the leg-cycle crank axis can be written as:

$$\tau_{e_l} \triangleq B_{e_l}u_{e_l}(t) \quad (9)$$

where $B_{e_l} \in \mathbb{R}_{\geq 0}$e represents the unknown, nonlinear relationship between the electric motor current and the resulting torque applied about the crank axis, and $u_{e_l}$ (t) represents the subsequently designed leg-cycle motor control input.

Substituting expressions (2)-(5), (7), and (9) into expression (1) and rearranging produces:

$$B_M u_s + B_{e_l}u_{e_l} = M_l\ddot{q}_l + b_{c_l}\dot{q}_l + d_{c_l} + V_l\dot{q}_l + G_l + P_l + d_{r_l} - \tau_{vol_l} \quad (10)$$

where the combination of the muscle torque efficiencies is represented by $B_M \triangleq \Sigma_{m\in M}B_m\sigma_m k_m$ and the system's inertial effects are represented by $M_l \triangleq J_{c_l} + M_{p_l}$. $G_l$ represents the gravitational effects, while $P_l$ represents the passive viscoelastic muscle forces. $d_{r_l}$ reflects the disturbances of the rider in the leg cycle.

Leg-cycle dynamics can be represented as depicted in the equation shown in FIG. 3. The split-crank cycle enables the right and left leg to drive the cycle independently, such that the modeled dynamics of FIG. 3 represent a single side of the system, where the FES human input torque is represented at 131, added to the motor input torque represented at 132, and added to the volitional efforts represented at 133. This is equal to the inertial effects (shown at 134) added to the centripetal-Coriolis effects (shown at 135), the damping at the cycle (shown at 136), the gravitational effects (shown at 137), the passive viscoelastic muscle forces (shown at 138), and the disturbances of the cycle and the rider (shown at 139). The angular position is shown as $q_l$, angular cadence (velocity) $\dot{q}_l$, which over time corresponds to angular acceleration $\ddot{q}_l$.

Dynamic Models—Master Controller System

The master controller system switched dynamics for one side (e.g., one side of a hand-cycle system) may be modeled by the system:

$$\tau_{e_{mc}} \triangleq \tau_{c_{mc}}(q_{mc},\dot{q}_{mc},\ddot{q}_{mc},t) + \tau_{r_{mc}}(q_{mc},\dot{q}_{mc},\ddot{q}_{mc},t) \quad (11)$$

where $q_{mc}$: $\mathbb{R}_{\geq 0} \rightarrow Q_{mc}$, denotes the angular position of the upper body crank, and $Q_{mc} \subseteq \mathbb{R}$ is the set of all possible measurable master system crank angles. The subscript "mc" references the master controller system. The measured angular velocity in the master controller system is denoted by $\dot{q}_{mc}$: $\mathbb{R}_{\geq 0} \rightarrow \mathbb{R}$ and the unmeasurable angular acceleration of the crank arm is denoted by $\ddot{q}_{mc}$: $\mathbb{R}_{\geq 0} \rightarrow \mathbb{R}$. Using a similar process as shown for the leg-cycle system and recognizing that the forces applied about the master controller axis by the master system operator, denoted by $\tau_{vol_h}$: $\mathbb{R}_{\geq 0}$, are purely volitional, the master controller system can be represented by:

$$B_{e_{mc}}u_{e_{mc}} + \tau_{vol_{mc}} = M_{mc}\ddot{q}_{mc} + b_{c_{mc}}\dot{q}_{mc} + d_{c_{mc}} + V_{mc}\dot{q}_{mc} + G_{mc} + P_{mc} + d_{r_{mc}} \quad (12)$$

where $B_{e_{mc}} \in \mathbb{R}_{\geq 0}$ represents the unknown, nonlinear relationship between the electric motor current and the resulting torque applied about the master controller axis and $u_{e_{mc}}(t)$ represents the designed master controller motor control input. The unknown, nonlinear inertial effects, centripetal-Coriolis effects, gravitational effects, and passive viscoelastic muscle forces in (12) are represented by $M_{mc}$:$Q_{mc} \rightarrow \mathbb{R}$, $V_{mc}$:$Q_{mc} \times \mathbb{R} \rightarrow \mathbb{R}$, $M_{mc}$:$G_{mc} \rightarrow \mathbb{R}$, and $P_{mc}$:$Q_{mc} \times \mathbb{R} \rightarrow \mathbb{R}$ respectively, and $d_{e_{mc}}$ and $d_{r_{mc}}$ denote the unknown cycle and rider disturbances about the master controller crank.

The dynamics of the master system controller can be modeled as depicted in FIG. 4, where the motor in put torque is shown as 141 added to the operator's volitional efforts at 142. On the other side of the equation, the inertial effects 143 are added to the centripetal-Coriolis effects at 144, the damping at the cycle at 145, the gravitational effects at 146, the passive viscoelastic muscle forces at 147, and the disturbances of the cycle and rider at 148.

System Properties

The switched leg-cycle system in (10) and the master controller system in (12) have the following properties and assumptions, where i={mc, 1}.

Property 1. $\frac{1}{2}M_i = V_i$

Property 2. $c_{\underline{M_i}} \leq M_i \leq c_{\overline{M}_i}$ where $c_{\underline{M_i}}$, $c_{\overline{M}_i} \in \mathbb{R}_{\geq 0}$ are known constants.

Property 3. $|V_i| \leq c_{V_i}|\dot{q}_i| \in \mathbb{R}_{\geq 0}$ where $c_{V_i}$ is a known constant.

Property 4. $|G_i| \leq c_{G_i} \in \mathbb{R}_{\geq 0}$ where $c_{G_i}$ is a known constant.

Property 5. $|P_i| \leq c_{P1_i} + c_{P2_i}|\dot{q}_i|$ where $c_{P1_i}$, $c_{P2_i} \in \mathbb{R}_{\geq 0}$ are known constants.

Property 6. $|b_{c_i}| \leq c_{b_i}$ where $c_{b_i} \in \mathbb{R}_{\geq 0}$ is a known constant.

Property 7. $|d_{c_i} + d_{r_i}| \leq c_{d_i} \in \mathbb{R}_{\geq 0}$ where $c_{d_i}$ is a known constant.

Property 8. $B_{\underline{e_i}} \leq B_{e_i} \leq B_{\overline{e}_i}$ where $B_{\underline{e_i}}$, $B_{\overline{e}_i} \in \mathbb{R}_{\geq 0}$ are known constants.

Property 9. The combined muscle efficiency $B_M$ has a lower bound $\forall m$ such that when $\Sigma_{m\in M}\sigma_m > 0$, $B_{\underline{M}} \leq B_M$ where $B_{\underline{M}} \in \mathbb{R}_{\geq 0}$.

Assumption 1. Due to physical human limitations, $q_h$ is sufficiently smooth (i.e., $q_{mc}$, $\dot{q}_{mc}$, $\ddot{q}_{mc} \in \mathcal{L}_\infty$) and the volitional torques produced by the participant are upper bounded such that $|\tau_{vol_i}| \leq c_{vol_i} \in \mathbb{R}_{\geq 0}$.

Control Development

Figure 5:
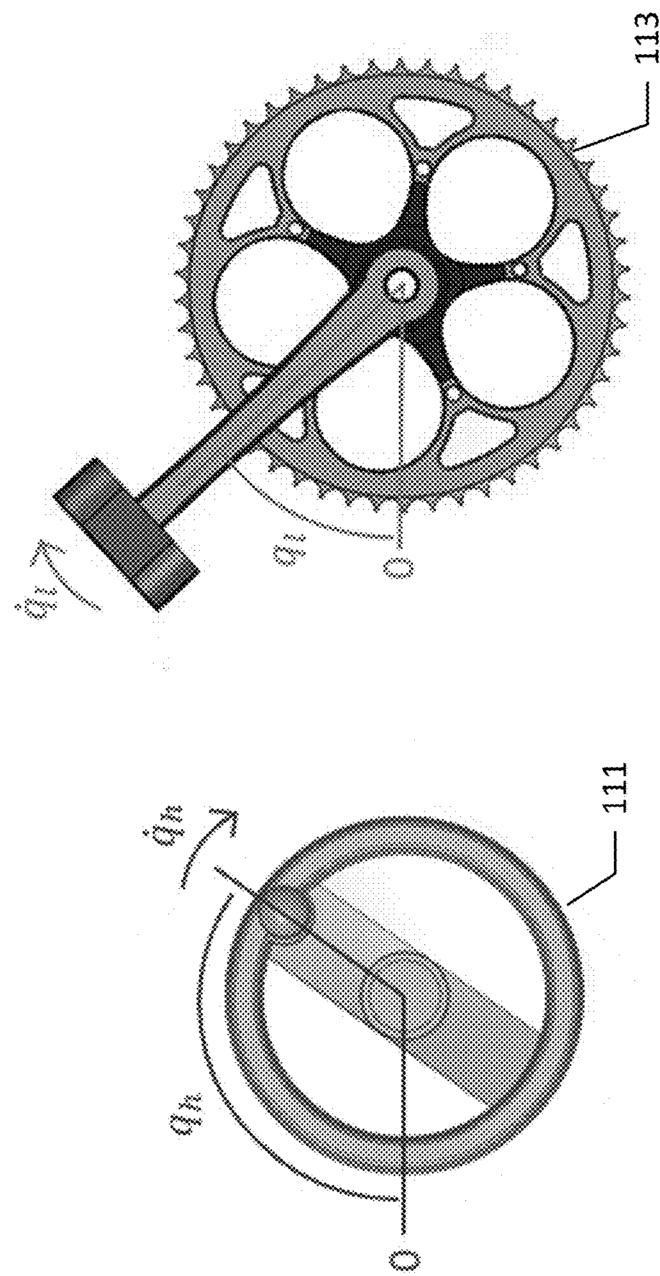
FIG. 5 illustrates teleoperation master controller represented by a hand operated valve wheel and its corresponding leg-cycle crank set with an original error factor according to an example embodiment of the present disclosure.

The control objective was to develop a strongly coupled telerobotic system, where the angular position of the master controller is tracked by the FES/motor actuated leg-cycle system. FIG. 5 illustrates teleoperation master controller represented by a hand operated valve wheel 111 and its corresponding leg-cycle crank set 113. To produce desired tracking objectives, an original error system is defined to quantify mismatch between the master controller and corresponding leg-cycle crank angles. An original residual error is also defined to introduce cadence tracking and to aid in the subsequent stability analysis.

With reference to FIG. 5 and an updated, improved error system and residual error, to quantify the objective, the mismatch between the leg and master controller, denoted by e: $\mathbb{R}_{\geq 0} \to \mathbb{R}$, and auxiliary error, denoted by r: $\mathbb{R}_{\geq 0} \to \mathbb{R}$, are defined as:

$$e_0 \triangleq \int_{t_0}^{t} q_{mc}(s) - q_l(s)ds \quad e_1 \triangleq \dot{e}_0 + \alpha_0 e_0 \tag{13}$$

The residual error is quantified through introduction of cadence tracking and aid in the subsequent stability analysis:

$$r \triangleq \dot{e}_1 + \alpha_1 e_1 \tag{14}$$

where $\alpha \in \mathbb{R}_{\geq 0}$ is a selectable constant.

Taking the time derivative of expression (14), multiplying by $M_l$, and using expression (13) yields:

$$M_l\dot{r} = M_l[\ddot{q}_{mc} - \ddot{q}_l + (\alpha_0+\alpha_1)(r-\alpha_1 e_1) + \alpha_0^2(e_1 - \alpha_0 e_0)] \tag{15}$$

Rearranging expressions (10) and (12) and substituting into expression (15) for $\ddot{q}_l$ and $\ddot{q}_{mc}$ gives:

$$M_l\dot{r} = \chi_1 - V_l r - e_1 - B_M u_s - B_{e_l} u_{e_l} M_l M_{mc}^{-1} B_{e_{mc}} u_{e_{mc}} \tag{16}$$

where the auxiliary term $\chi$: $\mathbb{R} \times \mathbb{R} \times \mathbb{R}_{\geq 0} \mathbb{R}$ is defined as:

$$\chi \triangleq M_l\alpha(r-\alpha e) + V_l(\dot{q}_{mc} + \alpha e) - \tau_{vol_l} + b_{c_l}(c - r + \alpha e) + G_l + P_l + e + d_{c_l} + d_{r_l} + M_{mc}^{-1}(-b_{c_{mc}}\dot{q}_{mc} - d_{c_{mc}} - V_{mc}\dot{q}_{mc} - G_{mc} - P_{mc} - d_{c_{mc}} + \pi_{vol_{mc}}$$

From Properties 2-7 and Assumption 1, can be upper bounded as:

$$\chi \leq c_1 + c_2\|z\| + c_3\|z\|^2 \tag{17}$$

where $z \in \mathbb{R}^2$ is defined as $z \triangleq [e\ r]^T$ and $c_1, c_2, c_3 \in \mathbb{R}_{\geq 0}$ are known constants.

Based on expressions (14) and (16) and the subsequent stability analysis, the switched FES control input is designed as:

$$u_s = \sigma_s(k_1 r + [k_2 + k_3\|z\| + k_4\|z\|^2]\mathrm{sgn}(r)) \tag{18}$$

where $k_1, k_2, k_3, k_4 \in \mathbb{R}_{\geq 0}$ are selectable constant control gains and the switching signal, $\sigma_s$: $Q_l \to \{0,1\}$, for leg stimulation is designed as:

$$\sigma_s \triangleq \begin{cases} 1 \text{ if } q_l \in Q_{FES} \\ 0 \text{ if } q_l \notin Q_{FES} \end{cases}. \tag{19}$$

Position tracking can be difficult on the split-crank bicycle, particularly in the hamstring stimulation region due to the lack of assistance being provided from the quadriceps femoris muscle group from the opposing leg in a standard joined-crank cycle. This difficulty often leads to saturated stimulation of the hamstring muscle group causing rapid onset of fatigue, poor tracking, and potential participant discomfort. A switching signal for leg-cycle motor effort, $\sigma_e$: $Q_l \times \{0,1\} \to [0,1]$, is designed as:

$$\sigma_e \triangleq \begin{cases} 1 & \text{if } q_l \notin Q_{FES} \\ \prod_{m \in \mathcal{M}} (1 - \beta_m \sigma_m) & \text{if } q_l \in Q_{FES} \end{cases}, \tag{20}$$

where $\beta_m \in [0,1]$, $\forall_m \in \mathcal{M}$ are constants selected to provide variable motor assistance throughout the FES regions. Based on (14) and (16) and the subsequent stability analysis, the switched leg-cycle motor controller is designed as $$u_{e_l} = \sigma_e(k_5 r + [k_6 + k_7\|z\| + k_8\|z\|^2]\mathrm{sgn}(r)) \tag{21}$$

where $k_5, k_6, k_7, k_8 \in \mathbb{R}_{\geq 0}$ are selectable constant control gains. According to one example embodiment, to ensure resistivity of the master controller motor effort relative to the operator, in the sense that the master controller motor should only be applied to resist, or slow, the angular velocity of the master controller rather than act to pull the master controller toward the leg trajectory, a switching signal, $\sigma_{mc}$: $\mathbb{R} \times \mathbb{R} \to \{0,1\}$ is designed as:

$$\sigma_{mc} \triangleq \begin{cases} 1, & \text{if } \dot{e}_0\dot{q}_{mc} > 0 \\ 0, & \text{if } \dot{e}_0\dot{q}_{mc} \leq 0 \end{cases} \tag{22}$$

where, if the system is operating using a standard forward rotation ($\dot{q}_{mc} > 0$) and the angular position of the legs is trailing behind the angular position of the master controller operator (e>0), then motor effort will be applied about the master controller crank. Likewise, if the system is operating with reversed rotation ($\dot{q}_{mc} < 0$) and the angular position of the legs is larger than the angular position of the master controller operator (e<0), then the motor effort will be applied. The switched master controller error feedback motor controller is designed as:

$$u_{e_{mc}} = -\sigma_{mc} k_9 \dot{e}_0 = -\sigma_{mc} k_9(q_{mc} - q_l) \tag{23}$$

Substituting expression (18), (21), and (23) into expression (19) produces the closed-loop error system:

$$\begin{aligned} M_l\dot{r} = \chi - V_l r - e - B_M\sigma_s k_1 r - \\ B_{e_l}\sigma_e k_5 r - B_M\sigma_s[k_2 + k_3\|z\| + k_4\|z\|^2]sgn(r) - \\ B_{e_l}\sigma_e[k_6 + k_7\|z\| + k_8\|z\|^2]sgn(r) - M_l M_{mc}^{-1} B_{e_{mc}} k_9 \sigma_{mc} e \end{aligned} \tag{24}$$

Stability Analysis

A Lyapunov-based stability analysis is provided herein for two cases; when $q_l \notin Q_{FES}$ and when $q_t \in Q_{FES}$. A theorem is presented for each case to evaluate the stability of the switched leg-cycle system. Switching times are denoted by $t\{t_n^i\}$, $i \in \{s, e\}$, $n \in \{0,1,2, \ldots\}$, where each $t_n^i$ represents the n-th time that the leg-cycle system switches to the stimulation region (denoted by i=s) or the electric motor only region (denoted by i=e). For teleoperation master system (i.e., the master controller) to be considered stable, it must be shown that all system states are bounded.

Let V: $\mathbb{R} \to \mathbb{R}_{\geq 0}$ be a positive, definite, radially unbounded common Lyapunov function candidate defined as:

$$V = \tfrac{1}{2}M_l r^2 + \tfrac{1}{2}e^2 \tag{25}$$

Such that:

$$\lambda_l\|z\|^2 \leq V \leq \lambda_2\|z\|^2 \tag{26}$$

where $\lambda_1=\min\{\frac{1}{2}, \frac{1}{2}c_{\underline{M}_l}\}$ and $\lambda_2=\max\{\frac{1}{2}, \frac{1}{2}c_{\overline{M}_l}\}$. Due to the discontinuous nature of the FES control input and motor controllers, the time derivative expression (25) exists almost everywhere (a.e.) within $t\in[t_0, \infty)$ and $$\dot{V}(z) \overset{a.e.}{\in} \dot{\tilde{V}}(z),$$

where $\dot{\tilde{V}}$ is the generalized time derivative of expression (25). Let z(t) for $t\in[t_0, \infty)$ be a Filippov solution to the differential inclusion $\dot{z}\in K[h](z)$, where h: $\mathbb{R}^2\rightarrow\mathbb{R}^2$ is defined as $h\triangleq[\dot{e}\ \dot{r}]^T$. Solving expression (14) for $\dot{e}$, using expressions (17), (21), (23), and (24), Property 1, and canceling common terms produces:

$$\dot{\tilde{V}} \subseteq \chi r - B_M\sigma_s k_1 r^2 - B_{e_l}\sigma_e k_5 r^2 - M_l M_{mc}^{-1} B_{e_{mc}} k_9 \sigma_{mc} e r - \alpha e^2 - B_M\sigma_s\|r\|(k_2 + k_3\|z\| + k_4\|z\|^2) - B_{e_l}\sigma_e\|r\|(k_6 + k_7\|z\| + k_8\|z\|^2). \tag{27}$$

The first theorem showing that the system is stable in the non-FES simulation regions of the crank cycle is as follows. For $q_l\notin Q_{FES}$, where $t\in[t_n^{\,e}, t_{n+1}^{\,s})$, the position and cadence error systems are globally exponentially stable in the sense that:

$$\|z(t)\| \le \sqrt{\frac{\lambda_2}{\lambda_1}}\,\|z(t_n^e)\|\exp\left[-\frac{\min(\psi_1,\psi_2)}{2\lambda_2}(t-t_n^e)\right], \tag{28}$$

provided the following gain conditions are met:

$$k_6 > \frac{c_1}{B_{\underline{e}_l}},\ k_7 > \frac{c_2}{B_{\underline{e}_l}},\ k_8 > \frac{c_3}{B_{\underline{e}_l}}, \tag{29}$$

$$k_5 > k_9\frac{c_{\overline{M}_l}B_{\overline{e}_{mc}}}{2c_{\overline{M}_{mc}}B_{\overline{e}_l}} \tag{30}$$

$$\alpha > k_9\frac{c_{\overline{M}_l}B_{\overline{e}_{mc}}}{2c_{\overline{M}_{mc}}} \tag{31}$$

This is proven as follows. When a $q_l\notin Q_{FES}$ and $\sigma_e=1$. Eliminating $u_s$, using Properties 2 and 8, and recognizing that $\sigma_h\in\{0,1\}\forall t$, expression (27) becomes:

$$\dot{V} \overset{a.e.}{\le} \|r\|(c_1 + c_2\|z\| + c_3\|z\|^2) - B_{\underline{e}_l}k_5\|r\|^2 - B_{\underline{e}_l}\|r\|(k_6 + k_7\|z\| + k_8\|z\|^2) + \frac{c_{\overline{M}_l}}{c_{\underline{M}_{mc}}}B_{\overline{e}_{mc}}k_9\|r\|\,\|e\| - \alpha\|e\|^2. \tag{32}$$

Selecting the control gains as in expression (29) gives:

$$\dot{V} \overset{a.e.}{\le} -B_{\underline{e}_l}k_5\|r\|^2 - \alpha\|e\|^2 + \frac{c_{\overline{M}_l}}{c_{\underline{M}_{mc}}}B_{\overline{e}_{mc}}k_9\|r\|\,\|e\|. \tag{33}$$

By Young's Inequality, $$\dot{V} \overset{a.e.}{\le} -B_{\underline{e}_l}k_5\|r\|^2 - \alpha\|e\|^2 + \frac{k_9 c_{\overline{M}_l}B_{\overline{e}_{mc}}}{2c_{\underline{M}_{mc}}}(\|r\|^2 + \|e\|^2). \tag{34}$$

Selecting the gains $k_5$ and $\alpha$ as in expressions (30) and (31), respectively, and defining $\psi_1\triangleq k_5-$ $$k_9\frac{c_{\overline{M}_l}B_{\overline{e}_{mc}}}{2c_{\underline{M}_{mc}}B_{\underline{e}_{mc}}} \text{ and } \psi_2 \triangleq \alpha - k_9\frac{c_{\overline{M}_l}B_{\overline{e}_{mc}}}{2c_{\underline{M}_{mc}}}, \text{ then:} \tag{35}$$

$$\dot{V} \overset{a.e.}{\le} -\psi_1 r^2 - \psi_2 e^2,$$

is a negative definite function. Using expression (26) it can be shown that $$\dot{V} \overset{a.e.}{\le} -\frac{\min(\psi_1\psi_2)}{\lambda_2}V.$$

Solving the differential inequality, using expression (26), and solving for $\|z(t)\|$ yields expression (28). From expressions (25) and (35) it can be seen that e, $r\in\mathcal{L}_\infty$, $\forall t\in[t_n^{\,e}, t_{n+1}^{\,s})$. Thus, from expressions (18), (21), and (23), it can be seen that $u_s$, $u_{e_l}$, $u_{e_{mc}}\in\mathcal{L}_\infty$, $\forall t\in[t_n^{\,e}, t_{n+1}^{\,s})$, respectively.

A second theorem is used to demonstrate the success of example embodiments and that the system is stable in regions of the crank cycle where FES is active. For $q_l\in Q_{FES}$, where $t\in[t_n^{\,e}, t_{n+1}^{\,s})$, the position and cadence error systems are globally exponentially stable in the sense that:

$$\|z(t)\| \le \sqrt{\frac{\lambda_2}{\lambda_1}}\,\|z(t_n^s)\|\exp\left[-\frac{\min(\psi_2,\psi_3)}{2\lambda_2}(t-t_n^s)\right], \tag{36}$$

provided the following conditions are met:

$$k_2 > \frac{c_1}{B_{\underline{M}}},\ k_3 > \frac{c_2}{B_{\underline{M}}},\ k_4\frac{c_3}{B_{\underline{M}}}, \tag{37}$$

$$k_1 > k_9\frac{c_{\overline{M}_l}B_{\overline{e}_{mc}}}{2c_{\underline{M}_{mc}}B_{\underline{M}}}. \tag{38}$$

To prove this, when $q_l\in Q_{FES}$, $\sigma_s=1$, and $\sigma_e=\Pi_{m\in\mathcal{M}}(1-\beta_m\sigma_m)$ Using Properties 2 and 8. recognizing that $\sigma_h\in\{0,1\}\forall t$, expression (27) becomes:

$$\dot{V} \overset{a.e.}{\le} \|r\|(c_1 + c_2\|z\| + c_3\|z\|^2) - B_{\underline{M}}k_1\|r\|^2 - B_{\underline{M}}\|r\|(k_2 + k_3\|z\| + k_4\|z\|^2) - B_{\underline{e}_l}\left[\prod_{m\in\mathcal{M}}(1-\beta_m\sigma_m)\right]k_5\|r\|^2 - B_{\underline{e}_l}\left[\prod_{m\in\mathcal{M}}(1-\beta_m\sigma_m)\right]\|r\|(k_6 + k_7\|z\| + k_8\|z\|^2) - \alpha\|e\|^2 + \frac{k_9 c_{\overline{M}_l}B_{\overline{e}_{mc}}}{2c_{\underline{M}_{mc}}}\|r\|\,\|e\|. \tag{39}$$

Choosing the control gains as in expression (37) and recognizing that $0 \le \sigma_e \le 1 \forall t$, gives:

$$\dot{V} \overset{a.e.}{\leq} -B_{\underline{M}} k_1 \|r\|^2 - \alpha \|e\|^2 + \frac{k_9 c_{\overline{M}_l} B_{\overline{e}_{mc}}}{2 c_{\underline{M}_{mc}}} \left(\|r\|^2 + \|e\|^2\right). \tag{40}$$

Selecting the gains $\alpha$ and $k_1$ as in expressions (31) and (38), respectively, $$\psi_3 \triangleq k_1 - k_9 \frac{c_{\overline{M}_l} B_{\overline{e}_{mc}}}{2 c_{\underline{M}_h} B_{\underline{e}_{mc}}},$$

then:

$$\dot{V} \overset{a.e.}{\leq} -\psi_3 r^2 - \psi_2 e^2, \tag{41}$$

is a negative definite function. From expression (41), using similar methods as in the first theorem produces expression (36). From expressions (25) and (41) it can be seen that e, r $\in \mathcal{L}_\infty$, $\forall t \in [t_n^e, t_{n+1}^s)$. Thus, from expressions (18), (21), and (23), it can be seen that $u_s$, $u_{e_l}$, $u_{e_{mc}}$, $\in \mathcal{L}_\infty$, $\forall t \in [t_n^e, t_{n+1}^s)$, respectively.

From the above theorems, the equilibrium point z=0 of the combined leg and master controller system is globally exponentially stable ∀t in the sense that:

$$\|z(t)\| \le \sqrt{\frac{\lambda_2}{\lambda_1}} \|z(t_0)\| \exp\left[-\frac{\zeta}{2\lambda_2}(t - t_0)\right], \forall t. \tag{42}$$

To prove this, defining $\zeta \triangleq \min(\psi_1, \psi_2, \psi_3)$, from expressions (26), (35), and (41), and solving the resulting differential inequality, it can be shown that:

$$\dot{V} \overset{a.e.}{\leq} -\zeta \|z(t)\|^2 \overset{a.e.}{\leq} -\frac{\zeta}{\lambda_2} V,$$
$$V(t) \le V(t_0) \exp\left[-\frac{\zeta}{2\lambda_2}(t - t_0)\right]. \tag{43}$$

Using expression (26) and solving the differential inequality in expression (43) for $\|z(t)\|$ yields expression (42). Recalling that $$z \triangleq [er]^T, |e|, |r| \le \sqrt{\frac{\lambda_2}{\lambda_1}} \|z(t_0)\| \exp\left[-\frac{\zeta}{2\lambda_2}(t - t_0)\right],$$

$\forall t$. From expressions (18), (21), and (23), $u_s$, $u_{e_l}$, $u_{e_{mc}} \in \mathcal{L}_\infty$, $\forall t$.

Conclusion

The telerobotic master controller system described herein, in conjunction with the addition of variable motor assistance in unstimulated regions, improves FES rehabilitative cycling techniques by introducing coordinated motion between the upper and lower limbs, in the case where the rehabilitation participant is the master system operator, in a way that enables the rider to obtain feedback of the leg cycling capability and to have direct control over the desired cadence and position. To maintain coordination and positively influence a participant's neural plasticity, the telerobotic system is designed with variable motor assistance in the FES regions to ensure that it is strongly coupled. Lyapunov-based analysis techniques for switched systems are used to prove global exponential stability of the equilibrium point of the combined hand and leg-cycle systems provided that certain gain conditions are met.

Embodiments described herein further enable a physical therapist to operate the master controller remotely while experiencing force-feedback from the leg-cycle components, thus "feeling" where a patient may be experiencing difficulties in movement. The variable motor assistance provided through the FES regions may be modified to a function of the ratio between current stimulation intensity and maximum intensity. By doing so, the assistive motor effort increases if a muscle group approaches saturation levels, ultimately slowing the onset of muscle fatigue and increasing the duration of rehabilitation sessions through allowing the participant to adjust their cadence to reduce stimulation intensity and maintain their chosen level of comfort.

Figure 6:
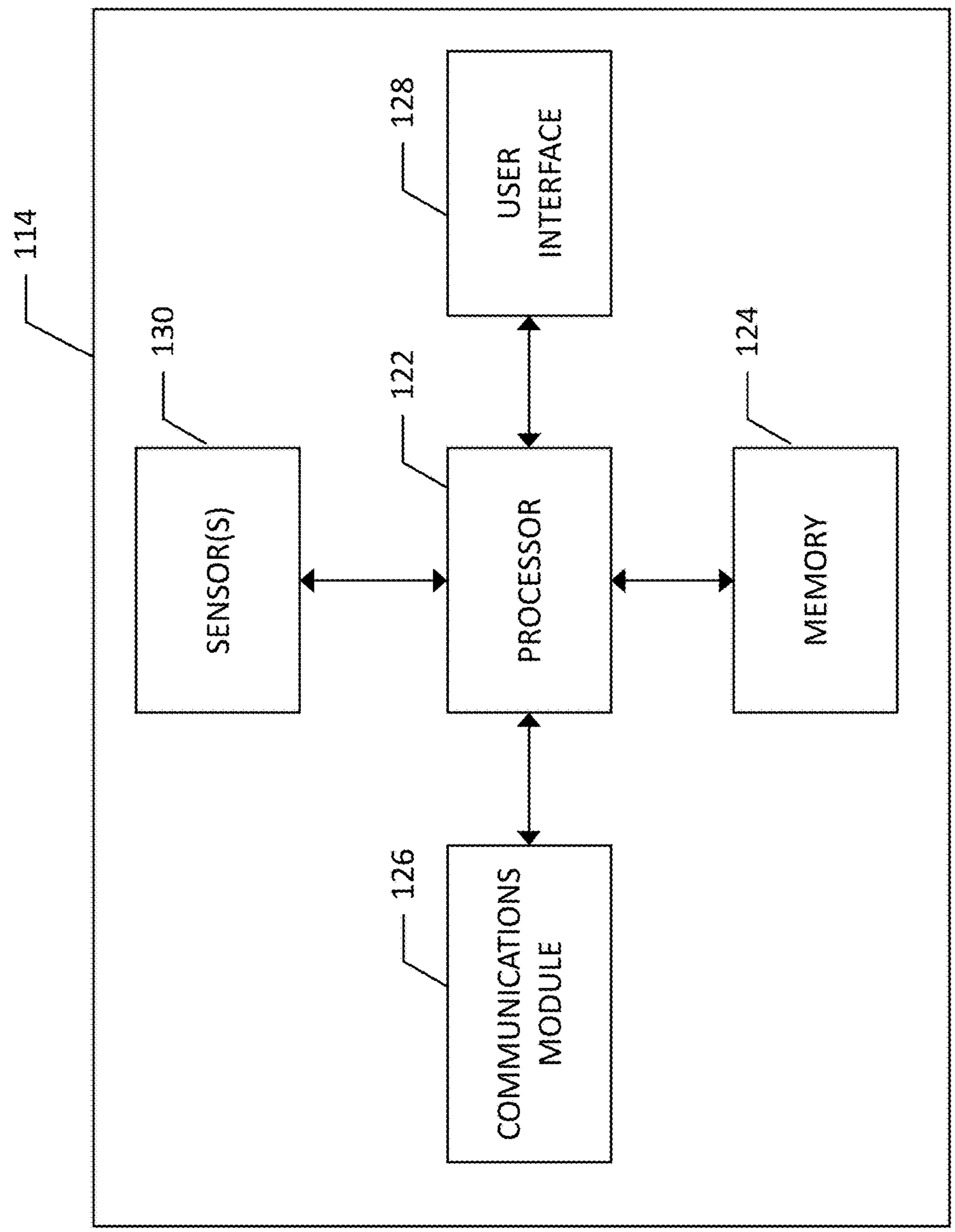
FIG. 6 is a schematic diagram of an example of a controller according to an example embodiment of the present disclosure.

FIG. 6 is a schematic diagram of an example of a controller 114 as shown in FIG. 1 that may be implemented to provide the bilateral teleoperation of a cycle as described herein. The controller 114 may include or otherwise be in communication with a processor 122, a memory device 124, a communications module 126 and a user interface 128. As such, in some embodiments, although devices or elements are shown as being in communication with each other, hereinafter such devices or elements should be considered to be capable of being embodied within the same device or element and thus, devices or elements shown in communication should be understood to alternatively be portions of the same device or element.

In some embodiments, the processor 122 (and/or co-processors or any other processing circuitry assisting or otherwise associated with the processor) may be in communication with the memory device 124 via a bus for passing information among components of the apparatus. The memory device 124 may include, for example, one or more volatile and/or non-volatile memories. In other words, for example, the memory device 124 may be an electronic storage device (e.g., a computer readable storage medium) comprising gates configured to store data (e.g., bits) that may be retrievable by a machine (e.g., a computing device like the processor). For example, the memory device 124 could be configured to buffer input data for processing by the processor 122. Additionally or alternatively, the memory device could be configured to store instructions for execution by the processor.

The processor 122 may be embodied in a number of different ways. For example, the processor 122 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. A multi-core processor may enable multiprocessing within a single physical package. Additionally or alternatively, the processor 122 may include one or more processors configured in tandem via the bus to enable independent execution of instructions, pipelining and/or multithreading. The processor may be embodied as a microcontroller having custom bootloader protection for the firmware from malicious modification in addition to allowing for potential firmware updates.

In an example embodiment, the processor 122 may be configured to execute instructions stored in the memory device 124 or otherwise accessible to the processor 122. Alternatively or additionally, the processor 122 may be configured to execute hard coded functionality. As such, whether configured by hardware or software methods, or by a combination thereof, the processor 122 may represent an entity (e.g., physically embodied in circuitry) capable of performing operations according to an embodiment of the present invention while configured accordingly. Thus, for example, when the processor 122 is embodied as an ASIC, FPGA or the like, the processor 122 may be specifically configured hardware for conducting the operations described herein. Alternatively, as another example, when the processor 122 is embodied as an executor of software instructions, the instructions may specifically configure the processor 122 to perform the algorithms and/or operations described herein when the instructions are executed. However, in some cases, the processor 122 may be a processor of a specific device (e.g., a head-mounted display) configured to employ an embodiment of the present invention by further configuration of the processor 122 by instructions for performing the algorithms and/or operations described herein. The processor 122 may include, among other things, a clock, an arithmetic logic unit (ALU) and logic gates configured to support operation of the processor 122. In one embodiment, the processor 122 may also include user interface circuitry configured to control at least some functions of one or more elements of the user interface 128.

The communications module 126 may include various components, such as a device or circuitry embodied in either hardware or a combination of hardware and software that is configured to receive and/or transmit data for communicating data between a physical therapist and a patient for teleoperation of the cycle as described herein. In this regard, the communications module 126 may include, for example, an antenna (or multiple antennas) and supporting hardware and/or software for enabling communications wirelessly. Additionally or alternatively, the communications module 126 may include the circuitry for interacting with the antenna(s) to cause transmission of signals via the antenna (s) or to handle receipt of signals received via the antenna(s). For example, the communications module 126 may be configured to communicate wirelessly such as via Wi-Fi (e.g., vehicular Wi-Fi standard 802.11p), Bluetooth, mobile communications standards (e.g., 3G, 4G, or 5G) or other wireless communications techniques. In some instances, the communications module 126 may alternatively or also support wired communication, which may communicate with a separate transmitting device (not shown). As such, for example, the communications module 126 may include a communication modem and/or other hardware/software for supporting communication via cable, digital subscriber line (DSL), universal serial bus (USB) or other mechanisms. For example, the communications module 126 may be configured to communicate via wired communication with other components of a computing device.

The user interface 128 may be in communication with the processor 122, such as the user interface circuitry, to receive an indication of a user input and/or to provide an audible, visual, mechanical, or other output to a user. As such, the user interface 128 may include, for example, one or more buttons, light-emitting diodes (LEDs), a display, a speaker, and/or other input/output mechanisms. The user interface 128 may also be in communication with the memory device 124 and/or the communications module 126, such as via a bus. The user interface 128 may include an interface with the cycle to provide the rehabilitative cycling through force feedback as described above.

The communications module 126 may facilitate communication between the master controller system 112, the FES muscle stimulation of the legs 116, and the leg-cycle crank shaft 118. Further, the communications module may facilitate communication from the master controller and leg-cycle systems to a rehabilitation therapist so the therapist can see and at least partially control the functionality of the cycle systems. The communications module 126 may be capable of operating in accordance with various first generation (1G), second generation (2G), 2.5G, third-generation (3G) communication protocols, fourth-generation (4G) communication protocols, fifth-generation (5G) communication protocols, Internet Protocol Multimedia Subsystem (IMS) communication protocols (e.g., session initiation protocol (SIP)), and/or the like. For example, a mobile terminal may be capable of operating in accordance with 2G wireless communication protocols IS-136 (Time Division Multiple Access (TDMA)), Global System for Mobile communications (GSM), IS-95 (Code Division Multiple Access (CDMA)), and/or the like. Also, for example, the mobile terminal may be capable of operating in accordance with 2.5G wireless communication protocols General Packet Radio Service (GPRS), Enhanced Data GSM Environment (EDGE), and/or the like. Further, for example, the mobile terminal may be capable of operating in accordance with 3G wireless communication protocols such as Universal Mobile Telecommunications System (UMTS), Code Division Multiple Access 2000 (CDMA2000), Wideband Code Division Multiple Access (WCDMA), Time Division-Synchronous Code Division Multiple Access (TD-SCDMA), and/or the like.

The controller may optionally include or be connected to one or more sensors 130, such as a force feedback sensor, a heart rate sensor, a body temperature sensor, or other physiological sensors that may sense information relating to the condition of an operator of the cycling systems.

Figure 7:
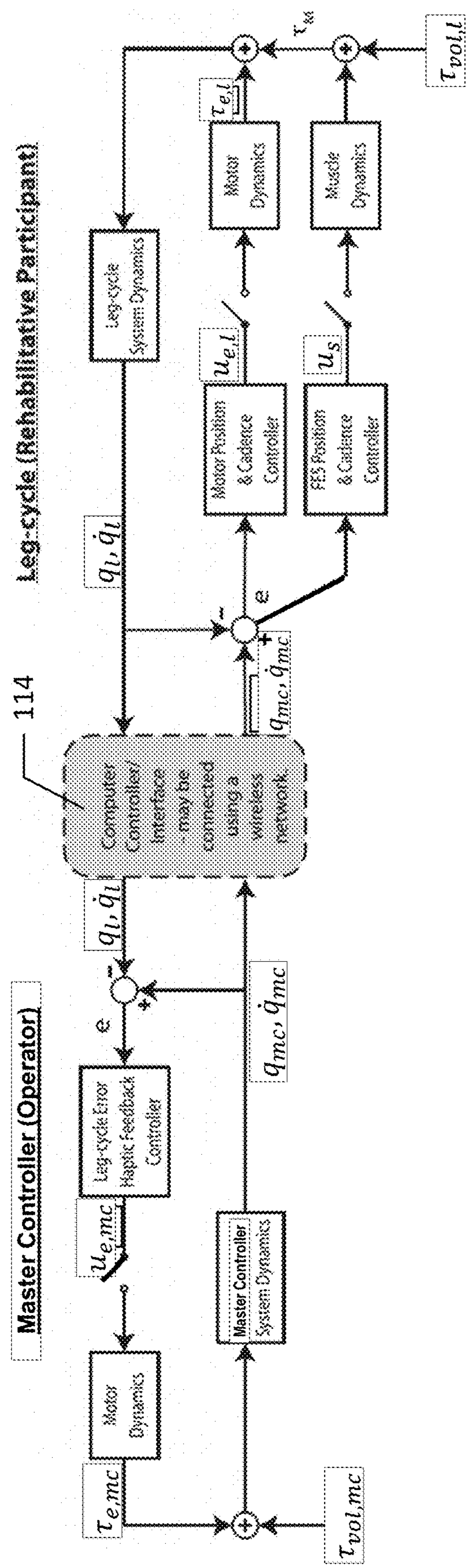
FIG. 7 is a block diagram representation of a bilateral teleoperated rehabilitative functional electrical stimulation cycling system according to an example embodiment of the present disclosure.

FIG. 7 is a block diagram representation of a bilateral teleoperated rehabilitative functional electrical stimulation cycling system according to an example embodiment of the present disclosure. The block diagram of FIG. 7 illustrates the bilateral teleoperation system with human-in-the-loop interaction on both sides of a computer interface (e.g., facilitated by the controller 114). The system is used to provide rehabilitation for people with neuromuscular conditions affecting lower body movement. According to example embodiments, an FES controller 114 works in line to make the participant's legs the primary actuator by automatically stimulating the necessary muscle groups to produce the desired trajectory while the motor works to assist the participant in regions of the crank cycle where muscle force is insufficient to produce rotation.

According to example embodiments described herein, a participant acts as a master system operator for the system, using the master controller to choose the desired performance at the legs. This exercise increases muscle mass and bone density, improves cardiovascular health, and coordinates the efforts of the hands and legs to improve neurological functions. A clinician may act as the master system operator in some embodiments, using either the master controller or the leg-cycle similar to the one used by the rehabilitative participant to choose the desired performance. The clinician could be remotely located from the participant in cases where circumstances limit the participant's ability to receive rehabilitation in a traditional clinical setting. The motor on the operator's side of the teleoperation may produce haptic feedback to the operator in response to any performance errors occurring on the participant's side. In this manner, the clinician is able to feel any areas of difficulty for the participant despite being remotely located.

According to an example embodiment, a remotely located therapist as an operator sets a cadence using a hand-cycle system as the master system. As the therapist is remotely located, there may be no physical or visual indication of how the rehabilitation participant's leg-cycle system (functioning as the slave system) is responding to the desired cadence of the hand-cycle. Therefore, haptic feedback (or motor resistance) is applied at the hand-cycle system to inform the remotely located therapist that the leg-cycle system is not keeping up with the desired performance. Similarly, in a scenario in which the rehabilitation participant is also acting as the master system operator, the rehabilitation participant may require haptic feedback to the hand-cycle system as they may not be able to feel how their legs are responding to the application of FES due to their neurological condition.

As shown in the block diagram of FIG. 7, and used in the expressions described above, signals of the system include resultant torque signals.

- $\tau_{vol,mc}$ is the volitional effort at the master controller (e.g., using hands);
- $\tau_{vol,l}$ is the volitional effort at the legs;
- $\tau_M$ is the combined simulated muscle torques and $\tau_{vol,l}$;
- $\tau_{e,mc}$ is the torque produced by the motor at the master controller;
- $\tau_{e,l}$ is the torque produced by the motor at the legs.

The resultant switched control effort is also illustrated in the block diagram as follows:

- $u_{e,mc}$ is the current applied to the motor at the master controller;
- $u_{e,l}$ is the current applied to the motor at the legs;
- $u_s$ is the stimulation intensity applied to the leg muscle groups.

The trajectories are also illustrated in the block diagram of FIG. 7 as follows:

- $q_{mc}$, $\dot{q}_{mc}$ is the angular position and velocity of the master controller, respectively;
- $q_l$, $\dot{q}_l$ is the angular position and velocity of the legs, respectively;
- e is the error between the desired and actual trajectories of the legs.

Figure 8:
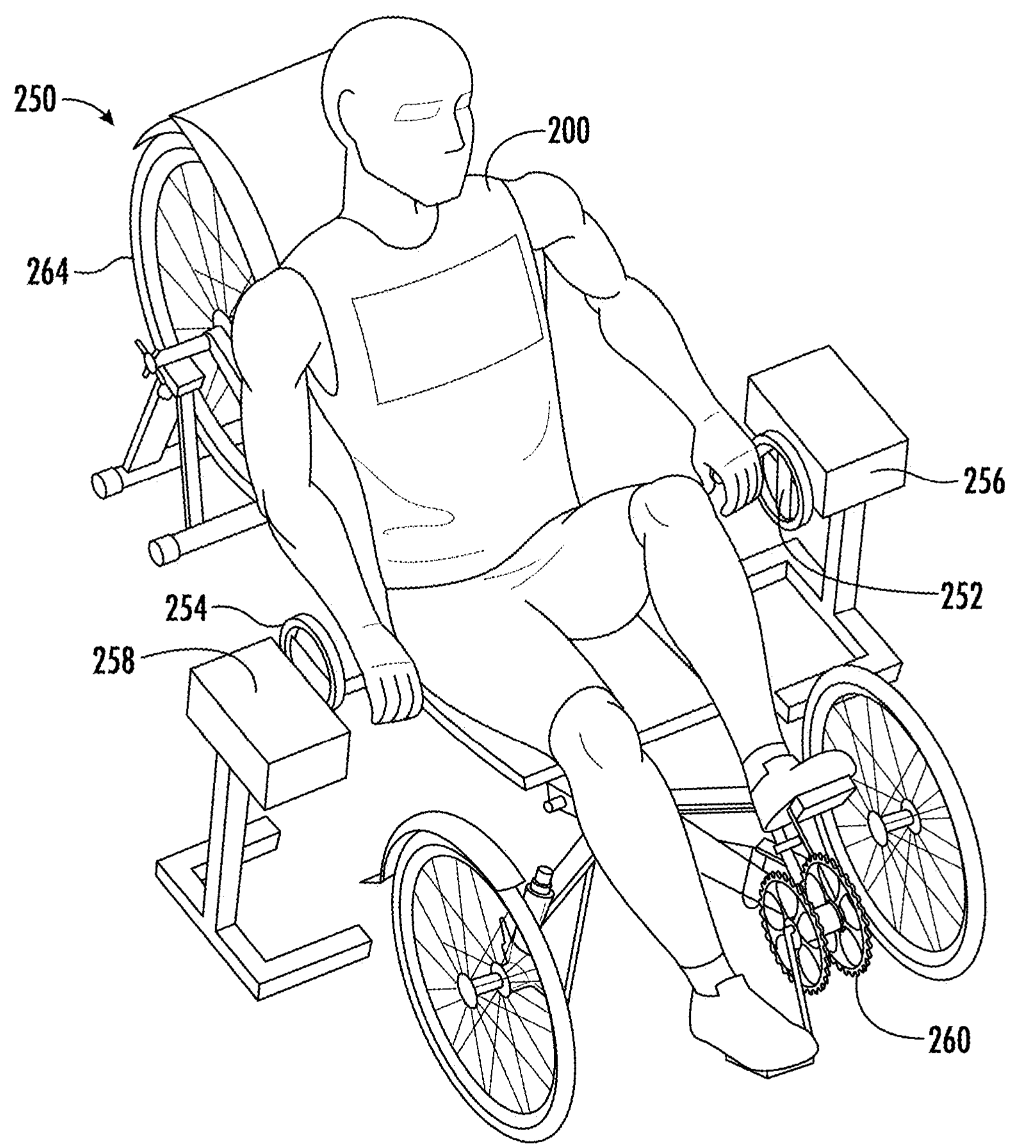
FIG. 8 is an illustration of a bilateral teleoperation system for a coordinated upper and lower body rehabilitative FES cycling according to an embodiment of the present disclosure.

FIG. 8 illustrates an example embodiment of a rehabilitative cycle 250 where a participant 200 is positioned to engage a hand-cycle system as the master controller system including a first hand cycle 252 and a second hand cycle 254, whereby the participant engages the hand-cycle system with both hands. The position of the first hand cycle 252 and second hand cycle 254 may be separated as illustrated in FIG. 8, or attached to one another positioned in front of the participant's chest for engagement by the hands of the participant. The rehabilitative cycle 250 further includes a leg-cycle system 260. The leg-cycle system 260 may be a split-crank leg-cycle system as described above whereby the participant may cycle each leg independently of the other. The hand-cycle system may operate similarly with the movement of one hand not driving movement of the other hand, for example.

The hand-cycle system may include a motor or generator attached to each hand cycle, such as a first motor 256 connected to the first hand cycle 252 and a second motor 258 connected to the second hand cycle 254. The motors or generators may be used to provide resistance to a user as they crank the hand-cycle system and may provide haptic feedback indicative of a difference in cadences as described above. The leg-cycle system 260 may similarly be attached to one or more motors, whereby the one or more motors may provide FES to the participant as described above and may provide resistance to a user as they cycle. Further, the motors described above may be used to provide torque readings from the participant's hand and leg motion driving the respective cycles. While the illustrated embodiment of FIG. 8 illustrates a recumbent tricycle form factor with the addition of the hand-cycle system and a suspended drive wheel 264 (which may be attached to the motor responsible for the leg-cycle system), embodiments may be entirely stationary with no cycle form factor, but instead having a hand-cycle system and a leg-cycle system coupled to motors and positioned for comfortable engagement by the participant 200.

Figure 9:
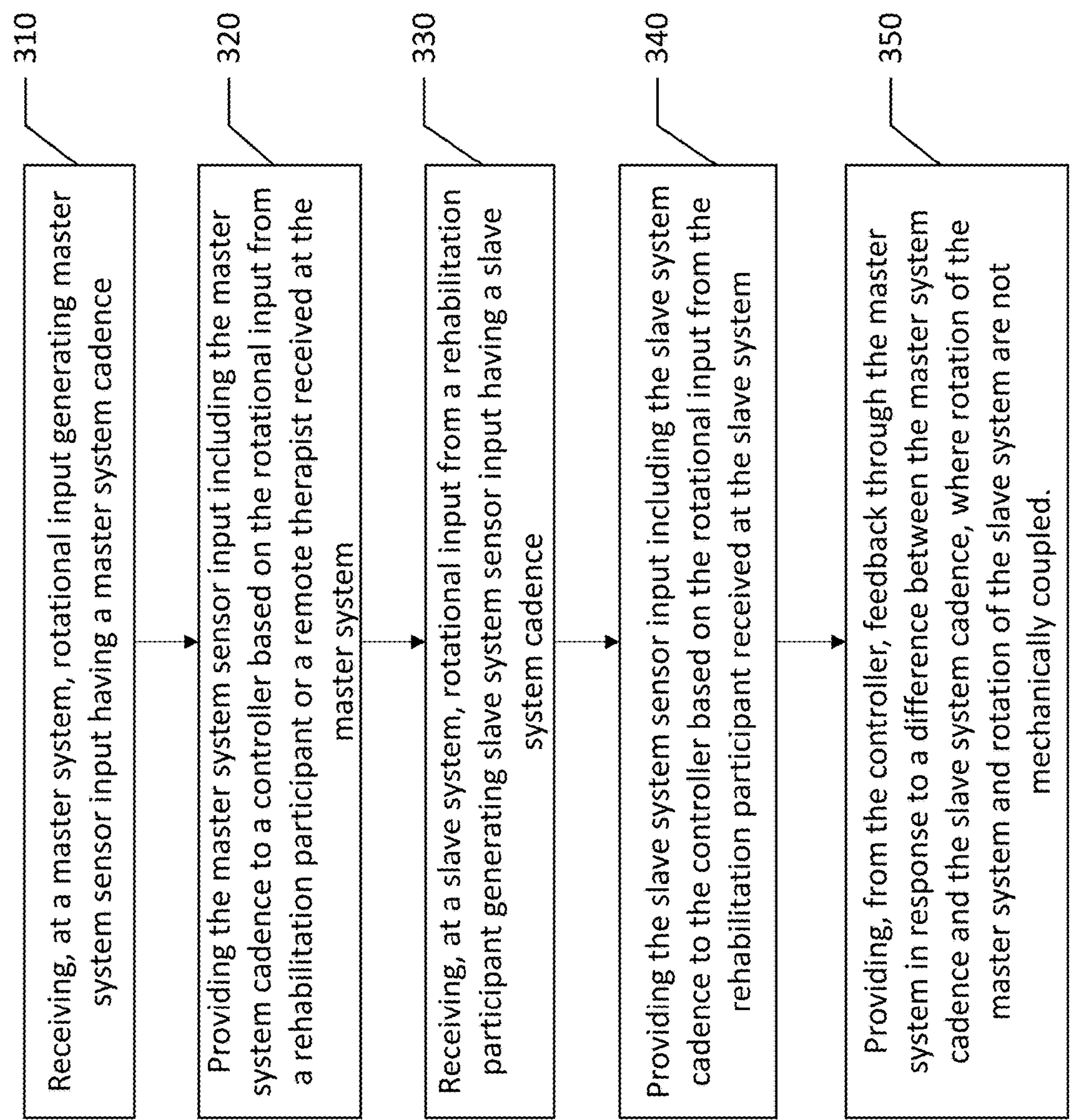
FIG. 9 is a flowchart of a method for teleoperated, motorized functional electric stimulation actuated rehabilitative cycling according to an example embodiment of the present disclosure.

FIG. 9 illustrates a flowchart of a method according to an example embodiment of the disclosure. It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by the memory device 124 of an apparatus employing an embodiment of the present invention and executed by the processor 122 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowcharts support combinations of means for performing the specified functions and combinations of operations for performing the specified functions for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

According to the flow chart of FIG. 9, rotational input generating master system sensor input having a master system cadence is received at 310. The master system sensor input including the master system cadence are provided, at 320, to a controller based on the rotational input from a rehabilitation participant or a remote therapist received at the master system. At 330, rotational input from a rehabilitation participant is received at a slave system generating slave system sensor input having a slave system cadence. The slave system sensor input including the slave system cadence is provided at 340 to the controller based on the rotational input from the rehabilitation participant received at the slave system. Feedback is provided at 350 from the controller through the master system in response to a difference between the master system cadence and the slave system cadence. Rotation of the master system and rotation of the slave system are not mechanically coupled.

In an example embodiment, an apparatus for performing the method of FIG. 9 above may comprise a processor (e.g., the processor 122) configured to perform some or each of the operations (310-350) described above. The processor may, for example, be configured to perform the operations (310-350) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 310-350 may comprise, for example, the processor 122 and/or a device or circuit for executing instructions or executing an algorithm for processing information as described above.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for rehabilitation comprising:

a master controller system, wherein the master controller system is configured to be driven by a master controller system operator's volitional efforts as rotational input at a master system cadence;

a leg-cycle system comprising a motor, wherein the leg-cycle system is configured to be driven by both functional electric stimulation of a rehabilitation participant and the motor; and a controller for receiving sensor input from the master controller system comprising the master system cadence and to control driving of the leg-cycle system by the functional electric stimulation of the rehabilitation participant and the motor responsive to sensor input from the master controller system and the master system cadence.

2. The system for rehabilitation of claim 1, wherein the controller is configured to apply a variable operator to the motor of the leg-cycle system during functional electric stimulation.

3. The system for rehabilitation of claim 1, wherein the controller controls driving of the leg-cycle system by the motor responsive to sensor input from the master controller system to generate position and velocity of the leg-cycle system based on a position and velocity of the master controller system.

4. The system for rehabilitation of claim 3, wherein the controller is configured to control application of resistive motor effort to the master controller system indicative of a difference between operation of the master controller system and the leg-cycle system by the rehabilitation participant.

5. The system for rehabilitation of claim 1, wherein the leg-cycle system is a split-crank leg-cycle system whereby two legs of a rehabilitation participant pedals the leg-cycle system independently.

6. The system for rehabilitation of claim 1, wherein the controller comprises a communications module for receiving control signals from the leg-cycle system at a remotely located therapist, wherein the control signals from the leg-cycle system provide haptic feedback to the remotely located therapist through the master controller system.

7. A method for rehabilitation comprising:

receiving, at a master system, rotational input generating master system sensor input having a master system cadence;

providing the master system sensor input including the master system cadence to a controller based on the rotational input from a rehabilitation participant or a remote therapist received at the master system;

receiving, at a slave system, rotational input from a rehabilitation participant generating slave system sensor input having a slave system cadence;

providing the slave system sensor input including the slave system cadence to the controller based on the rotational input from the rehabilitation participant received at the slave system;

providing, from the controller, feedback through the master system in response to a difference between the master system cadence and the slave system cadence, wherein rotation of the master system and rotation of the slave system are not mechanically coupled; and controlling the slave system with a motor of the slave system based on the master system cadence.

8. The method of claim 7, further comprising:

providing a signal to a motor coupled to the slave system based on rotational input at the master system.

9. The method of claim 7, further comprising:

transmitting feedback to the master system operated by the rehabilitation participant or the remote therapist; and receiving input to the controller to control haptic feedback to the master system.

10. The method of claim 7, further comprising:

transmitting feedback from the master system to the slave system; and receiving input to the controller to control motor input to the slave system.

11. The method of claim 7, wherein the master system comprises a hand-cycle system and wherein the slave system comprises a leg-cycle system.

12. A system for rehabilitation comprising:

a master system driven by a master system operator's volitional efforts, wherein the master system includes at least one of a hand-cycle system or a leg-cycle system;

a slave system driven by a participant's functional electric stimulation actuated muscle effort and a motor, wherein the slave system includes at least one of a hand-cycle system or a leg-cycle system; and a controller for receiving sensor input from the slave system and to control driving of the slave system by the motor responsive to sensor input from the master system.

13. The system for rehabilitation of claim 12, wherein the controller is configured to apply a variable operator to the motor of the slave system during functional electric stimulation.

14. The system for rehabilitation of claim 12, wherein the controller controls driving of the slave system by the motor and the functional electric stimulation actuated muscle effort responsive to sensor input from the master system to generate position and velocity of the slave system based on a position and velocity of the master system.

15. The system for rehabilitation of claim 14, wherein the controller controls resistive motor input applied to the master system indicative of a difference between operation of the master system and the slave system.

16. The system for rehabilitation of claim 12, wherein the slave system is a split-crank leg-cycle system whereby two legs of the participant pedal the leg-cycle system independently.

17. The system for rehabilitation of claim 12, wherein the controller comprises a communications module for communicating between the master system and the slave system, wherein the master system is located remotely from the slave system, and wherein the master system provides haptic feedback based on sensor input received at the slave system.

* * * * *